United States Patent
Zardi

(10) Patent No.: US 7,674,933 B2
(45) Date of Patent: Mar. 9, 2010

(54) METHOD FOR MODERNIZING A UREA PRODUCTION PLANT

(75) Inventor: Federico Zardi, Breganzona (CH)

(73) Assignee: Urea Casale S.A. (CH)

( * ) Notice: Subject to any disclaimer, the term of this patent is extended or adjusted under 35 U.S.C. 154(b) by 108 days.

(21) Appl. No.: 12/051,529

(22) Filed: Mar. 19, 2008

(65) Prior Publication Data

US 2008/0242890 A1 Oct. 2, 2008

(30) Foreign Application Priority Data

Mar. 29, 2007 (EP) .................... 07006566

(51) Int. Cl.
*C07C 273/04* (2006.01)
*B01J 10/02* (2006.01)
*F28D 7/00* (2006.01)

(52) U.S. Cl. ............................ 564/67; 564/66; 564/70; 564/71; 564/72; 422/188; 422/196; 422/200; 422/201; 422/202; 422/203

(58) Field of Classification Search .................... 564/66, 564/67, 70, 71, 72; 422/188, 196, 200, 201, 422/202, 203
See application file for complete search history.

(56) References Cited

U.S. PATENT DOCUMENTS 5,660,801 A 8/1997 Pagani et al.

FOREIGN PATENT DOCUMENTS

| EP | 0136764 | A2 | 4/1985 |
|---|---|---|---|
| EP | 0435008 | A1 | 7/1991 |
| EP | 1036787 | A1 | 9/2000 |
| EP | 1333918 | B1 | 8/2003 |

*Primary Examiner*—Peter G O'Sullivan
(74) *Attorney, Agent, or Firm*—Akerman Senterfitt

(57) ABSTRACT

A method for modernizing a urea production plant including a urea synthesis reactor, a stripping unit and at least one condensation unit. The method includes providing: means in the condensation unit for substantially condensing at least a portion of a flow comprising ammonia and carbon dioxide in vapor phase leaving the stripping unit; a second stripping unit; means for feeding a first portion of a reaction mixture flow comprising urea, carbamate and free ammonia in aqueous solution leaving the reactor to the first stripping unit; means for feeding a second portion of the reaction mixture flow leaving the reactor to the second stripping unit; and means for feeding at least a portion of a flow comprising ammonia and carbon dioxide in vapor phase leaving the second stripping unit directly to the synthesis reactor. A de-bottlenecking of the high-pressure section downstream of the synthesis reactor may be achieved, improving production capacity.

12 Claims, 2 Drawing Sheets

METHOD FOR MODERNIZING A UREA PRODUCTION PLANT

FIELD OF APPLICATION

The present invention relates to a method for the modernisation of a plant for urea production according to the process with stripping with carbon dioxide.

More specifically, the invention relates to a method for the modernization of a plant for urea production of the type comprising:

- a reactor for urea synthesis;
- means for feeding ammonia and carbon dioxide to the reactor for urea synthesis;
- a stripping unit with carbon dioxide for subjecting a reaction mixture comprising urea, carbamate and free ammonia in aqueous solution leaving the reactor to a treatment of partial decomposition of carbamate and partial separation of free ammonia, thus obtaining a flow comprising ammonia and carbon dioxide in vapour phase and a flow comprising urea and residual carbamate in aqueous solution, respectively;
- a recovery section for the flow comprising urea and residual carbamate in aqueous solution leaving the stripping unit for separating urea from the residual carbamate in aqueous solution;
- at least one condensation unit of the film type, comprising a tube bundle for subjecting to partial condensation the flow comprising ammonia and carbon dioxide in vapour phase leaving the stripping unit, thus obtaining a liquid flow comprising carbamate in aqueous solution and a gaseous flow comprising ammonia and carbon dioxide in vapour phase;
- means for respectively feeding the flow comprising carbamate in aqueous solution and the flow comprising ammonia and carbon dioxide in vapour phase to the reactor for urea synthesis;

In the following description. and enclosed claims, with the term "modernization", it is intended to mean the modification of a pre-existing plant with the purpose of improving its performance and obtaining, for example, an increase of the production capacity and/or of the conversion yield and/or a reduction of the energy consumption.

In the following description and enclosed claims, with the term "condensation unit of the film type", it is intended to mean an apparatus wherein the condensation of the gaseous phase occurs in a liquid film, flowing downwards inside a plurality of tubes in co-current with the gaseous flow. The liquid film flows in contact with the tube wall whereas the gaseous phase flows inside the tubes.

According to a further aspect, the present invention also relates to a process for urea production as well as to a plant for carrying out such process.

PRIOR ART

Methods for the modernization of existing plants for urea production according to the stripping process with carbon dioxide have been recently set forth in the field.

In particular, EP 1036787 discloses a method for the modernization of a plant for urea production as indicated above in which the flow comprising ammonia and carbon dioxide in vapour phase coming from the stripping unit is split in a minor portion and in a major portion. The minor portion is sent directly to the synthesis reactor for controlling the reaction temperature inside it (thermal balance, while the major portion is sent to the condensation unit.

In addition, the pre-existing condensation unit of the film type is modified and in particular it is transformed in a condensation unit of the submerged type for subjecting to substantially total condensation the major portion of the flow comprising ammonia and carbon dioxide in vapour phase leaving the stripping unit, so obtaining a flow comprising urea and carbamate in aqueous solution.

In this way, higher conversion yield and higher production capacity are obtained thanks to the fact that a condensation unit of the submerged type is used which provides a higher efficiency than that of a condensation unit of the film type.

In the following description and enclosed claims, with the term "condensation unit of the submerged type", it is intended to mean an apparatus wherein the liquid phase fills (submerges) the tube, bundle and wherein the condensation of the gaseous phase occurs by passing through such liquid phase. In other words, in this case, the condensation unit operates having the tube bundle's tubes full of liquid, which is different from the condensation unit of the film type wherein the tubes are substantially empty.

Although advantageous on several aspects, there is a constant need in this field to provide further methods for modernizing the above-mentioned plant which are able to meet specific needs, while obtaining at the same time high production capacity and/or conversion yield at low investment and operation costs, as well as low energy consumption.

SUMMARY OF THE INVENTION

The technical problem underlying the present invention is therefore that of providing a method for the modernization of a plant for urea production according to the stripping process with carbon dioxide which allows to obtain high production capacity and conversion yield, implies low energy consumption and investment costs and is technically easy to be implemented.

According to the present invention, this problem is solved by a method of the aforementioned type, which further comprises the step of:

- providing in said at least one condensation unit means for subjecting to substantially total condensation at least a portion of a flow comprising ammonia and carbon dioxide in vapour phase leaving said stripping unit, obtaining a flow comprising urea and carbamate in aqueous solution, and which is characterised by comprising the steps of:

- providing a second stripping unit,
- providing means for feeding a first portion of the flow of reaction mixture comprising urea, carbamate and free ammonia in aqueous solution leaving the reactor to said stripping unit;
- providing means for feeding a second portion of the flow of reaction mixture comprising urea, carbamate and free ammonia in aqueous solution leaving the reactor to said second stripping unit; and
- providing means for feeding at least a portion of a flow comprising ammonia and carbon dioxide in vapour phase leaving said second stripping unit directly to the synthesis reactor.

The main advantage of the method of modernization according to the present invention is that of obtaining a substantial de-bottlenecking of the equipment of the high-pressure section downstream the synthesis reactor, which is particularly significant in plants of large installations.

In this regard, the present invention allows, on the one hand, to remarkably increase the exchange coefficient and therefore the efficiency of the pre-existing condensation unit and, on the other hand, to remarkably improve the efficiency and capacity of processing (stripping) the reaction mixture leaving the synthesis reactor, the latter by simply adding a new stripping unit downstream the reactor.

This results in a greater overall production capacity and conversion yield than those of prior art plants.

In addition, the above result is achieved in a simple and effective way, with minimum interventions in the high-pressure synthesis section of the existing plant, and with limited energy consumption.

Accordingly, the investment, implementation and operation costs required by the method of modernization according to the invention are limited/low as well.

In this regard, it should be noted that, thanks to the present invention, the pre-existing condensation unit is not upgraded nor replaced with new apparatuses, but advantageously preserved requiring only small internal modifications of the condensation unit (s) in such a way to obtain a substantially total condensation of the gaseous phase fed therein. Furthermore, the addition of a stripping unit downstream the synthesis reactor requires lower investment costs than those required by modifying the existing stripping unit in such a way to increase its capacity.

Accordingly, the investment, implementation and operation costs required by the method of modernization according to the invention are low as well.

Furthermore, thanks to the fact of providing means for feeding at least a portion of the flow comprising ammonia and carbon dioxide in vapour phase leaving the new stripping unit directly to the synthesis reactor, the portion of reactants in gaseous phase necessary for controlling the temperature inside the reactor (thermal balance) is not made any longer to pass through the condensation unit together with le liquid phase, as in the prior art. So doing, the condensation unit can be modified internally in such a way to permit the substantial condensation of all the gaseous reactants fed to it (coming from the pre-existing stripping unit and/or the new stripping unit) and hence to operate at the maximum efficiency obtainable.

According to a preferred embodiment of the invention, the method of modernization further comprises the step of:
  providing means for feeding the entire flow comprising ammonia and carbon dioxide in vapour phase leaving said stripping unit directly to the bottom of said at least one condensation unit;
  providing means for feeding the entire flow comprising ammonia and carbon dioxide in vapour phase leaving said second stripping unit directly to the reactor.

In this embodiment, no split of a gaseous phase is performed but conversely it is performed only a split of a liquid phase (reaction mixture leaving the reactor) which is advantageously simpler and allows a better control on the portions of liquid phase to be split.

Furthermore, in this embodiment, the reaction mixture comprising urea, carbamate and free ammonia in aqueous solution is preferably fed in a minor portion to the second (new) stripping unit and in a major portion to the (pre-existing) stripping unit. The amount of minor portion of the reaction mixture to be fed to the second stripping unit depends on the operating conditions of the plant and is chosen in such a way to assures a proper portion of reactants in gaseous phase coming from the second stripping unit to the synthesis reactor for controlling the temperature inside it (thermal balance).

Preferably, said minor portion fed to the new stripping unit is about a third (⅓) of the reaction mixture comprising urea, carbamate and free ammonia in aqueous solution and said major portion fed to the existing stripping unit is about two-thirds of said reaction mixture.

According to further aspect of the present invention, the above second stripping unit is of the type using carbon dioxide as a stripping agent and the method of modernization further comprises the step of:
  providing means for sending a portion of feed carbon dioxide to said second stripping unit.

According to a further aspect, the present invention relates to a process for producing urea characterized in that it comprises the steps of:
  reacting ammonia and carbon dioxide in a reaction space, obtaining a reaction mixture comprising urea, carbamate and free ammonia in aqueous solution;
  feeding a first portion of the reaction mixture to a stripping section with carbon dioxide and subjecting said first portion to a treatment of partial decomposition of carbamate and partial separation of free ammonia, obtaining a first flow comprising ammonia and carbon dioxide in vapour phase and a first flow comprising urea and residual carbamate in aqueous solutions;
  feeding a second portion of the reaction mixture to a second stripping section and subjecting said second portion to a treatment of partial decomposition of carbamate and partial separation of free ammonia, obtaining a second flow comprising ammonia and carbon dioxide in vapour phase and a second flow comprising urea and residual carbamate in aqueous solution
  feeding said first flow and said second flow comprising urea and residual carbamate in aqueous solution to an urea recovery section;
  feeding at least a portion of said first flow comprising ammonia and carbon dioxide in vapour phase to at least one condensation unit and subjecting said at least a portion to a substantially total condensation, obtaining a flow comprising urea and carbamate in liquid phase;
  feeding at least a portion of said second flow comprising ammonia and carbon dioxide in vapour phase directly to the reaction space, and
  feeding the flow comprising urea and carbamate in liquid phase to the reaction space.

According to a further aspect, the present invention further relates to a plant intended for carrying out the aforesaid process for producing urea, comprising:
  a reactor for urea synthesis;
  means for feeding ammonia and carbon dioxide to the reactor for urea synthesis;
  a first stripping unit with carbon dioxide for subjecting a first portion of the reaction mixture comprising urea, carbamate and free ammonia in aqueous solution leaving the reactor to a treatment of partial decomposition of carbamate and partial separation of free ammonia, obtaining a first flow comprising ammonia and carbon dioxide in vapour phase and a first flow comprising urea and residual carbamate in aqueous solution;
  at least one condensation unit of the submerged type;
  and which is characterised in that it further comprises:
  a second stripping unit,
  means for feeding a first portion of the flow of reaction mixture comprising urea, carbamate and free ammonia in aqueous solution leaving the reactor to said first stripping unit;
  means for feeding a second portion of the flow of reaction mixture comprising urea, carbamate and free ammonia in aqueous solution leaving the reactor to said second stripping unit, and means for feeding at least a portion of a flow comprising ammonia and carbon dioxide in vapour phase leaving said second stripping unit directly to the synthesis reactor.

According to the invention, the plants intended for carrying out the process for urea production can be realised both ex-novo or by modifying pre-existing plants, so as to obtain an increase in the production capacity and in some cases an improved performance from the point of view of energy consumption.

Further features and advantages of the present invention will appear more clearly from the following non limiting description of two embodiments of the method of modernization and of the urea synthesis process according to the invention, made with reference to the attached drawings.

DETAILED DESCRIPTION OF A PREFERRED EMBODIMENT

Figure 1:
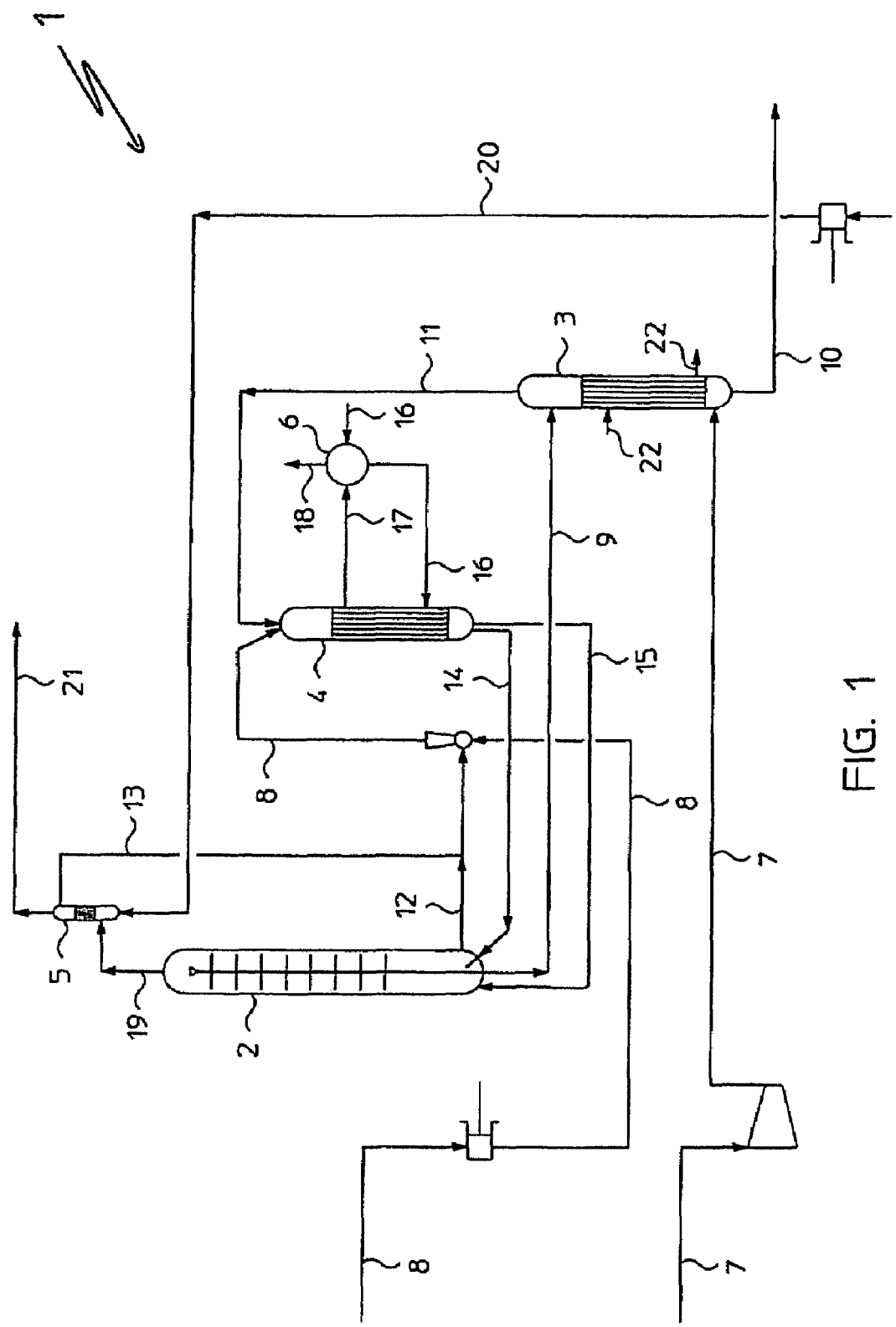
FIG. 1 illustrates schematically and partially a plant for urea production according to the stripping process with carbon dioxide of the prior art.

Just to simplify the disclosure of the present invention, only a portion of a plant for urea production is schematically represented in FIG. 1 and more precisely the high pressure synthesis section (synthesis loop), the remaining sections being not significant for the comprehension of the present invention.

Further on, specific reference to the per se conventional connecting ducts of the various parts of the plant described hereinbelow and illustrated in FIG. 1, will be made only when strictly necessary.

With reference to FIG. 1, an existing plant for urea production according to the stripping process with carbon dioxide and featuring the recycle of the reactants to the reaction space, is indicated in whole with reference numeral 1.

Plant 1, and more specifically the high pressure synthesis section, comprises a reactor 2 (or reaction space) for urea synthesis, a stripping unit 3 with carbon dioxide, a condensation section comprising a vertical condensation unit 4 of the film type and a washing unit 5 of the passivating agents and other possible substances inert to the reaction.

Moreover, plant 1 comprises a recovery section for the urea produced, not represented in FIG. 1, and an apparatus 6 for the separation of the steam produced by the cooling liquid fed to the condensation unit 4.

The reactor 2 operates usually at a temperature comprised between 180 and 185° C. with a molar ratio $NH_3/CO_2$ comprised between 2.8 and 3.0, a molar ratio $H_2O/CO_2$ comprised between 0.4 and 0.5, and a conversion yield comprised between 58 and 60%.

The (isobaric) process pressure in the synthesis section of FIG. 1 is usually comprised between 140 and 145 bar. Such pressure is usually indicated in the urea synthesis processes as "high" pressure, as compared with the terms "medium" (about 18 bar) and "low" (3-4 bar) pressure, respectively, used in the field to indicate the pressure in the sections downstream the synthesis loop.

In FIG. 1, with the numerals 7-21 respective means for feeding the various flows to the apparatuses of plant 1 for urea production are generally indicated.

Such, feeding means comprises pipelines or connecting ducts, pumps, compressors, ejectors and other devices of known type, generally employed in such kind of plants, and therefore they will not be further described in the following description.

Generally, in the present description and in the enclosed claims, and where it is not differently indicated, by the terms: "feeding, connecting or extraction means", it is intended to mean pipelines, connecting lines or ducts, pumps, compressor, ejectors or other devices of known type, which are used for transporting a liquid or gaseous flow from a location to another one in the plant.

More in particular, with 7 and 8 are indicated respective means for feeding to the stripping unit 3 a gaseous flow comprising feed carbon dioxide, and to the condensation unit 4 a flow comprising feed ammonia (in liquid phase).

The feed carbon dioxide sent to the stripping unit 3 through means 7 is employed as stripping agent of a reaction mixture comprising urea, carbamate and free ammonia in aqueous solution leaving the reactor 2 and fed to the unit 3 through means 9.

The stripping unit 3 is of the film type with an external heating with steam. Means for feeding and extracting steam for the heating of the stripping unit 3 on the shell side are generally indicated with 22.

The reaction mixture flowing downwards in the unit 3 in countercurrent with the gaseous flow comprising carbon dioxide is subjected to a treatment of partial decomposition of carbamate and partial separation of the free ammonia, obtaining a flow comprising ammonia and carbon dioxide in vapour phase and a flow comprising urea and residual carbamate in aqueous solution.

The flow comprising urea and residual carbamate in aqueous solution is extracted from the bottom of the stripping unit 3 and sent to the urea recovery section (non represented) through the feeding means 10.

The gaseous flow obtained in the stripping unit 3 and comprising also water in addition to ammonia and carbon dioxide, flows out from an upper end of such unit 3 and is fed to an upper end of the condensation unit 4 through feeding means 11.

The condensation unit 4 is of the vertical film type for subjecting to partial condensation all the flow comprising ammonia and carbon dioxide in vapour phase coming from the unit 3 through means 11.

Further on, the flow comprising feed ammonia is fed to the upper end of the condensation unit 4 through means 8 together with a recycled flow comprising ammonia and carbamate in aqueous solution. Recycled ammonia and carbamate in aqueous solution are fed into the flow comprising feed ammonia through feeding means 13. Connecting means 12 are also provided between the reactor 2 and the feeding means 13.

The partial condensation of the gaseous phase takes place as a result of the contact of such phase with the liquid phase, flowing in co-current downwards inside a plurality of tubes of a tube bundle enclosed in a shell of the condensation unit 4.

The phase comprising ammonia and carbon dioxide in gaseous phase, as well as the phase comprising carbamate in aqueous solution are hence separately sent from the bottom of the condensation unit 4 to the reactor 2, for urea synthesis through respective feeding means 14, 15.

The heat produced during the partial condensation of the flow comprising ammonia and carbon dioxide in vapour phase inside the unit 4, is removed by making a cooling liquid, i.e. water, to flow through the tube bundle—on the shell side—producing recovery steam (generally at 4.5 absolute bar).

The water flow is fed on the shell side to the condensation unit 4 through means 16, and extracted from such unit through means 17.

The water flow coming out of the unit 4, and comprising also the steam produced by indirect heat exchange with the process fluids flowing inside the condensation unit 4 on the tubes side, is fed through means 17 to the apparatus 6 for the separation of the steam produced from the water. This water is thus recycled through means 16 to the condensation unit 4 on the shell side, whereas the steam is extracted from the separation apparatus 6 through means 18.

In the technical language of the field, the separation apparatus 6 is also indicated with the term "steam drum".

In order to protect the apparatuses of the high pressure synthesis section from corrosion, the plant 1 further comprises the possibility of flowing one or more passivating agents, for example oxygen or air, inert to urea synthesis reaction, through such devices.

To this end, means are generally provided for feeding a gaseous flow, comprising the passivating agents, to the stripping unit 3 and from such stripping unit to the urea synthesis reactor 2, passing through the condensation unit 4.

In the example of FIG. 1, the passivating agents are directly mixed with the gaseous flow comprising feed carbon dioxide, therefore the aforesaid means for feeding the gaseous flow comprising passivating agents corresponds to feeding means 7.

Moreover, the gaseous flow comprising carbon dioxide fed to the stripping unit 3 through the means 7 contains a certain amount of other inert substances, for example 1-3% in volume, which, together with the passivating agents, pass through the various apparatuses of the high pressure synthesis section.

The flow of inert substances passes through the urea synthesis reactor 2 entraining a part of the unreacted ammonia and carbon dioxide in vapour phase, and is thus fed through means 19 from an upper end of the reactor 2 to the washing unit 5.

In the washing unit 5, ammonia and carbon dioxide in vapour phase are condensed by means of a washing flow comprising—in the example of FIG. 1—carbamate in aqueous solution coming from the urea recovery section (not represented) and fed to the unit 5 through means 20.

From the washing unit 5, the extraction of the passivating agents and of the inert substances in general from the high pressure synthesis section takes place through means 21, whereas the washing flow suitably enriched in ammonia and carbon dioxide is sent to the condensations unit 4 through means 13.

Figure 2:
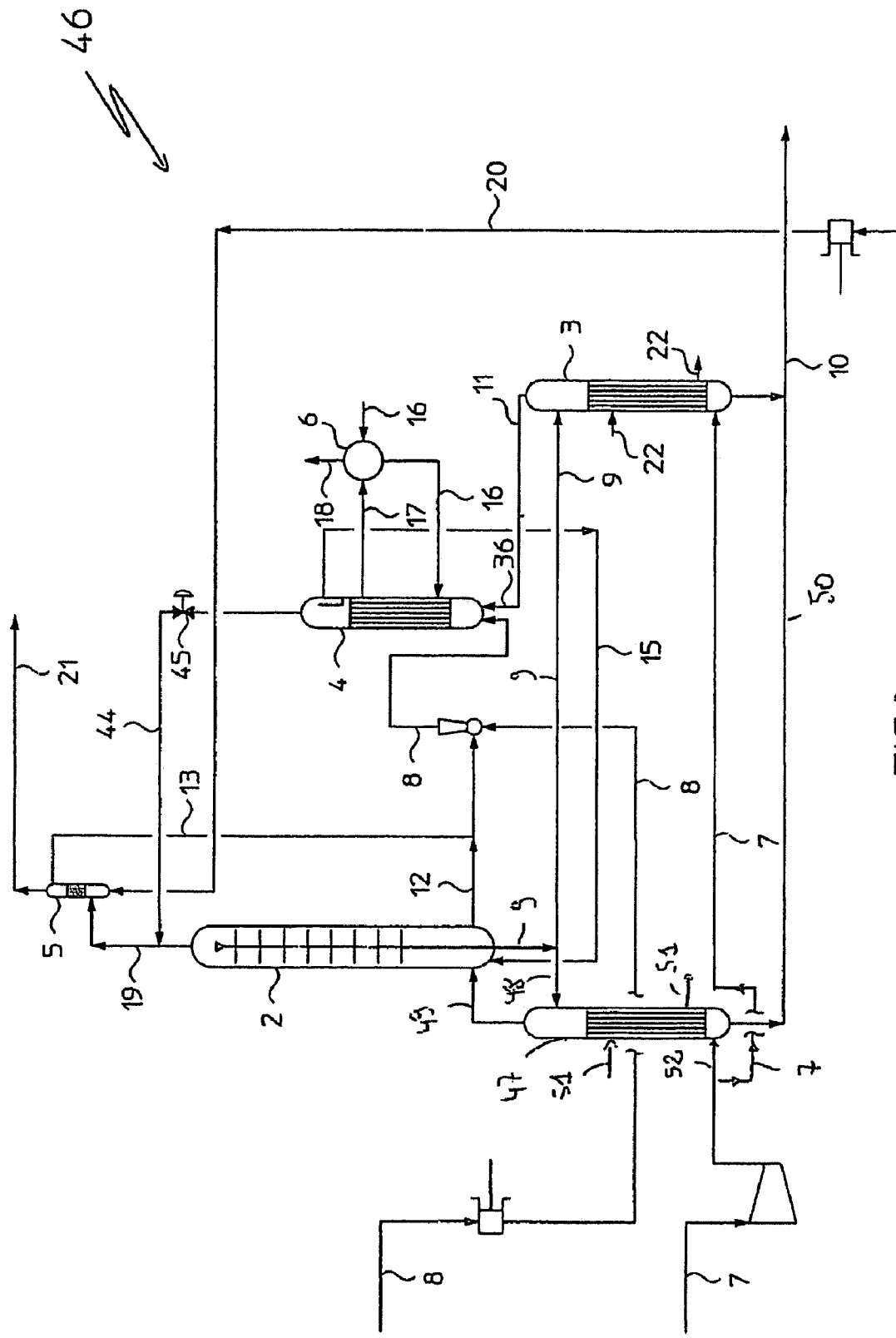
FIG. 2 illustrates schematically and partially a plant for urea production according to the stripping process with carbon dioxide realised by the modernization of the plant of FIG. 1 in accordance with an embodiment of the method of modernization according to the invention.

With reference to FIG. 2, the plant for urea production of FIG. 1 is advantageously represented suitably modified according to a preferred embodiment of the method of modernization of the present invention.

The plant resulting from the method of modernization according to said preferred embodiment of the invention is globally indicated with 46.

In FIG. 2, the details of plant 46 equivalent as for structure and operation to those illustrated in FIG. 1 will be indicated with the same reference numerals and will not be described again.

Thanks to the present invention, the condensation unit 4 is advantageously modified in its internal so as to permit a substantially total condensation of the gaseous flow comprising ammonia and carbon dioxide coming from the stripping unit 3 in a simple and effective way.

In other words, the existing vertical condensation unit of the film type is advantageously transformed in a vertical condensation unit of the "submerged" type, i.e. with the tube bundle full of condensation liquid, remarkably improving the efficiency of such unit and thus its capacity. Moreover, this change allows to increase the residence time of formation carbamate in the condensation unit 4, which partially reacts in urea.

Suitable means for transforming a condensation unit of the "film type" in a condensation unit of the "submerged type" is well known in the art. Preferred means is that disclosed in EP 1036787 and/or EP 1333918 which are incorporated herein by reference in this regard.

In addition, according to the embodiment of FIG. 2, means 11 of the existing plant of FIG. 1 are modified and means 36 are provided for feeding the flow comprising ammonia and carbon dioxide in vapour phase from the stripping unit 3 to the bottom of the condensation unit 4. Means 36 comprises for example a connection duct. Furthermore, the means 8 of the pre-existing plant of FIG. 1 are modified so as to feed the recycled flow comprising ammonia and carbamate solution in aqueous solution and feed ammonia to the bottom of the condensation unit 8.

In the condensation unit 4, the condensation liquid comprising carbamate in aqueous solution and ammonia is advantageously made to circulate inside the tube bundle with a termosiphon like motion. The flow comprising ammonia and carbon dioxide in vapour phase is instead fed through means 36 into the lower space near a lower end of the tube bundle of the condensation unit 4.

In doing so, ammonia and carbon dioxide in vapour phase pass through the condensation unit 4 upwards—in co-current with the condensation liquid—gurgling inside the tubes full of liquid of the tube bundle and thus with a considerable exchange coefficient on the tubes side.

Furthermore, according to the present method of modernization, a second stripping unit 47 is provided downstream the synthesis reactor 2.

In addition, means 9 are used for feeding a first portion of the flow of reaction mixture comprising urea, carbamate and free ammonia in aqueous solution leaving the synthesis reactor 2 to the per-existing stripping unit 3, and means 48 are provided for feeding a second portion of the flow of reaction mixture comprising urea, carbamate and free ammonia in aqueous solution leaving the synthesis reactor 2 to the second stripping unit 47.

In the present example, the second stripping unit 47 employs a portion of feed carbon dioxide as a stripping agent for the second portion of the reaction mixture comprising urea, carbamate and free ammonia in aqueous solution leaving the reactor 2. Consequently, suitable means 52 are provide for feeding a portion of feed carbon dioxide to the second stripping agent.

The stripping unit 47 is of the film type with an external heating with steam. Means for feeding and extracting steam for the heating of the stripping unit 47 on the shell side are generally indicated with 51.

Of course, according to an alternative embodiment (not shown), the second stripping unit 47 may employ heat instead of carbon dioxide as stripping agent. The heat may be provided by a suitable heating fluid, for example steam, flowing through the tube bundle of the stripping unit 47 on the shell side.

According to the method of modernization of the present invention, means 49 are also provided for feeding the second flow comprising ammonia and carbon dioxide in vapour phase leaving the second stripping unit 47 directly to the synthesis reactor 2. In this way, the reaction temperature inside the synthesis reactor 2 is controlled around optimal values for high conversion yield (thermal balance).

Furthermore, the method of modernization according to the present embodiment of the invention further provides means 50 for feeding the second flow comprising urea and residual carbamate in aqueous solution leaving the second stripping unit 47 to the urea recovery section (not shown).

In particular, in this embodiment, the second flow comprising urea and residual carbamate in aqueous solution leaving the second stripping unit 47 is mixed with the flow comprising urea and residual carbamate in aqueous solution leaving the pre-existing striping unit 3 and the resulting mixture flow is sent to the urea recovery section.

The scheme of FIGS. 2 represents only a preferred embodiment of modernization of existing plants for urea production according to the present invention and nothing prevents new plants to be realised in an advantageous way according to the teachings of the present invention.

In this regard, the advantages described with reference to the modernization of existing plants recur in the plants realised ex-novo as well, with the exception of the investment costs that are, of course, much higher for a new plant.

Thanks to the plant of FIG. 2 obtained after the modernization of an existing plant or realized ex-novo, it is advantageously possible to carry out the process for urea production described and claimed in the enclosed claims 5-7.

In particular, such a process is characterized in that a first portion of the reaction mixture comprising urea, carbamate and free ammonia coming from the reactor 2 is fed to a stripping section 3 with carbon dioxide where it is subjected to a treatment of partial decomposition of carbamate and partial separation of free ammonia, obtaining a first flow comprising ammonia and carbon dioxide in vapour phase and a first flow comprising urea and residual carbamate in aqueous solution;

In addition, a second portion of said reaction mixture is fed to the second stripping section 47 where it is subjected to a treatment of partial decomposition of carbamate and partial separation of free ammonia, obtaining a second flow comprising ammonia and carbon dioxide in vapour phase and a second flow comprising urea and residual carbamate in aqueous solution The first flow and said second flow comprising urea and residual carbamate in aqueous solution leaving the stripping unit 3 and the second stripping unit 47 are sent to an urea recovery section.

Instead, at least a first portion of the second flow comprising ammonia and carbon dioxide in vapour phase leaving the stripping unit 47 is fed directly to the reactor 2 for the thermal balance while at least a portion of the first flow comprising ammonia and carbon dioxide in vapour phase leaving the stripping unit 3 is fed to the condensation unit 4 where it is subjected to a substantially total condensation, obtaining a flow comprising urea and carbamate in liquid phase. The flow comprising urea and carbamate in liquid phase obtained in the condensation unit 4 is then recycled to the reactor 2.

In particular, according to a preferred embodiment of the process of the invention (FIG. 2), the condensation unit 4 is fed with the entire first flow comprising ammonia and carbon dioxide in vapour phase leaving the stripping section 3 while the reactor 2 is fed with the entire second flow comprising ammonia and carbon dioxide in vapour phase leaving the second stripping section 47.

In addition, the reaction mixture comprising urea, carbamate and free ammonia in aqueous solution leaving the reactor 2 is preferably fed in a minor portion to the second stripping unit 47 and in a major portion to the stripping unit 3.

Preferably, said minor portion fed to the second stripping unit 47 is about a third (⅓) of the reaction mixture comprising urea, carbamate and free ammonia leaving the reactor 2 and said major portion fed to the stripping unit 3 is about two-thirds of said reaction mixture.

The advantages attained with the process according to the present invention are various. In particular it is worth stressing that such process allows to obtain—simply and effectively—high conversion yields and therefore high production capacity, especially in large installation where it is operated a substantial de-bottlenecking of the equipments of the high-pressure loop downstream the synthesis reactor. Further on, its realisation is technically easy, with low energy consumption and investment costs.

Finally, the scope of protection defined by the method of modernization according to the present invention shall be considered as being extended—beside the modification of existing structures—also to the particular case of a replacement—because of wear—of the existing condensation unit with a new unit of the submerged type. This specific case occurs whenever the existing unit is at the end of its operating life and does not guarantee a reliable and lasting operation any more.

What is claimed is:

1. Method for the modernisation of a plant for urea production of the type comprising:

a reactor for urea synthesis;

means for feeding ammonia and carbon dioxide to the reactor for urea synthesis;

a stripping unit with carbon dioxide for subjecting a reaction mixture comprising urea, carbamate and free ammonia in aqueous solution leaving the reactor to a treatment of partial decomposition of carbamate and partial separation of free ammonia, thus obtaining a flow comprising ammonia and carbon dioxide in vapour phase and a flow comprising urea and residual carbamate in aqueous solution, respectively;

a recovery section for the flow comprising urea and residual carbamate in aqueous solution leaving the stripping unit for separating urea from the residual carbamate in aqueous solution;

at least one condensation unit of the film type, for subjecting to partial condensation said flow comprising ammonia and carbon dioxide in vapour phase leaving said stripping unit, thus obtaining a liquid flow comprising carbamate in aqueous solution and a gaseous flow comprising ammonia and carbon dioxide in vapour phase;

means for respectively feeding the flow comprising carbamate in aqueous solution and the gaseous flow comprising ammonia and carbon dioxide in vapour phase to said reactor for urea synthesis, said modernization method further comprising the step of:

providing in said at least one condensation unit means for subjecting to substantially total condensation at least a portion of a flow comprising ammonia and carbon dioxide in vapour phase leaving said stripping unit, obtaining a flow comprising urea and carbamate in aqueous solution, and being characterized by comprising the steps of:

providing a second stripping unit, providing means for feeding, a first portion of the flow of reaction mixture comprising urea, carbamate and free ammonia in aqueous solution leaving the reactor to said stripping unit;

providing means for feeding a second portion of the flow of reaction mixture comprising urea, carbamate and free ammonia in aqueous solution leaving the reactor to said second stripping unit; and providing means for feeding at least a portion of a flow comprising ammonia and carbon dioxide in vapour phase leaving said second stripping unit directly to the synthesis reactor.

2. Method according to claim 1, wherein it further comprises the steps of:

providing means for feeding the entire flow comprising ammonia and carbon dioxide in vapour phase leaving said stripping unit to the bottom of said at least one condensation unit;

providing means for feeding the entire flow comprising ammonia and carbon dioxide in vapour phase leaving said second stripping unit directly to the reactor.

3. Method according to claim 1, wherein it further comprises the step of:

providing means for feeding the flow comprising urea and residual carbamate in aqueous solution leaving said second stripping unit to said urea recovery section.

4. Method according to claim 1, wherein said second stripping unit is of the type using carbon dioxide as a stripping agent and in that it further comprises the step of:

providing means for sending a portion of feed carbon dioxide to said second stripping unit.

5. Process for producing urea wherein it comprises the steps of:

reacting ammonia and carbon dioxide in a reaction space, obtaining a reaction mixture comprising urea, carbamate and free ammonia in aqueous solution;

feeding a first portion of the reaction mixture to a stripping section with carbon dioxide and subjecting said first portion to a treatment of partial decomposition of carbamate and partial separation of free ammonia, obtaining a first flow comprising ammonia and carbon dioxide in vapour phase and a first flow comprising urea and residual carbamate in aqueous solution;

feeding a second portion of the reaction mixture to a second stripping section and subjecting said second portion to a treatment of partial decomposition of carbamate and partial separation of free ammonia, obtaining a second flow comprising ammonia and carbon dioxide in vapour phase and a second flow comprising urea and residual carbamate in aqueous solution feeding said first flow and said second flow comprising urea and residual carbamate in aqueous solution to an urea recovery section;

feeding at least a portion of said first flow comprising ammonia and carbon dioxide in vapour phase to the at least one condensation unit and subjecting, said at least a portion to a substantially total condensation, obtaining a flow comprising urea and carbamate in liquid phase;

feeding at least a portion of said second flow comprising ammonia and carbon dioxide in vapour phase directly to the reaction space, and feeding the flow comprising urea and carbamate in liquid phase to the reaction space.

6. Process according to claim 5, wherein said first flow comprising ammonia and carbon dioxide in vapour phase coming from the stripping unit is fed to the at least one condensation unit and said second flow comprising ammonia and carbon dioxide in vapour phase coming from said second stripping unit is fed to the reaction space.

7. Process according to claim 5, wherein said second portion of reaction mixture comprising urea, carbamate and free ammonia in aqueous solution fed to the second stripping section is a minor portion of the total flow of reaction mixture leaving the reaction space.

8. Process according to claim 7, wherein said minor portion fed to the second stripping unit is about one third of the total flow of reaction mixture leaving the reaction space.

9. Plant for urea production, comprising:

a reactor for urea synthesis;

means for feeding ammonia and carbon dioxide to the reactor for urea synthesis;

a first stripping unit with carbon dioxide for subjecting a first portion of the reaction mixture comprising urea, carbamate and free ammonia in aqueous solution leaving the reactor to a treatment of partial decomposition of carbamate and partial separation of free ammonia, obtaining a first flow comprising ammonia and carbon dioxide in vapour phase and a first flow comprising urea and residual carbamate in aqueous solution;

at least one condensation unit of the submerged type; wherein it further comprises:

a second stripping unit, means for feeding a first portion of the flow of reaction mixture comprising urea, carbamate and free ammonia in aqueous solution leaving the reactor to said first stripping unit;

means for feeding a second portion of the flow of reaction mixture comprising urea, carbamate and free ammonia in aqueous solution leaving the reactor to said second stripping unit, and means for feeding at least a portion of a flow comprising ammonia and carbon dioxide in vapour phase leaving said second stripping unit directly to the synthesis reactor.

10. Plant according to claim 9, wherein it comprises:

means for feeding the flow comprising ammonia and carbon dioxide in vapour phase leaving said stripping unit directly to said at least one condensation unit of the submerged type, and means for feeding the flow comprising ammonia and carbon dioxide in vapour phase leaving said second stripping unit directly to the reactor.

11. Plant according to claim 9, wherein it further comprises:

means for feeding the flow comprising urea and residual carbamate in aqueous solution leaving said second stripping unit to said urea recovery section.

12. Plant according to claim 9, wherein said second stripping unit is of the type using carbon dioxide as a stripping agent and in that it further comprises:

means for sending a portion of feed carbon dioxide to said second stripping unit.

* * * * *